(12) United States Patent
Gage

(10) Patent No.: US 6,520,976 B1
(45) Date of Patent: Feb. 18, 2003

(54) MODULAR HAND CONTROL FOR PNEUMATIC RESECTING TOOL

(75) Inventor: Gary B. Gage, Arlington, TX (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/303,781

(22) Filed: Apr. 30, 1999

(51) Int. Cl.⁷ .............................................. A61B 17/32
(52) U.S. Cl. ...................................... 606/170; 606/180
(58) Field of Search .......................... 606/79, 170, 171, 606/180; 433/125; 604/22

(56) References Cited

U.S. PATENT DOCUMENTS

| | | | |
|---|---|---|---|
| RE27,032 E | * 1/1971 | Hall | ........................... 606/180 |
| 3,712,386 A | 1/1973 | Peters | |
| 3,752,241 A | 8/1973 | Bent | |
| 4,530,357 A | 7/1985 | Pawloski et al. | |
| 4,541,423 A | 9/1985 | Barber | |
| 5,352,234 A | 10/1994 | Scott | |
| 5,439,005 A | 8/1995 | Vaughn | |
| 5,478,093 A | 12/1995 | Eibl et al. | |
| 5,505,737 A | 4/1996 | Gosselin | |
| 5,549,634 A | 8/1996 | Scott et al. | |
| 5,569,256 A | 10/1996 | Vaughn et al. | |
| 5,741,263 A | 4/1998 | Umber et al. | |

\* cited by examiner

*Primary Examiner*—Kevin T. Truong
(74) *Attorney, Agent, or Firm*—Haynes & Boone, LLP

(57) ABSTRACT

Devices and methods are described to rapidly and easily install a control device in a resecting tool system. The motor portion of the resecting tool can be readily separated from the air conduit to which it is attached. In a preferred embodiment, modular hand-operated control is then inserted between the air conduit and motor and interconnected with both components. The modular hand-control provides a housing with an actuatable lever, or handle, which controls an internal valve assembly.

32 Claims, 4 Drawing Sheets

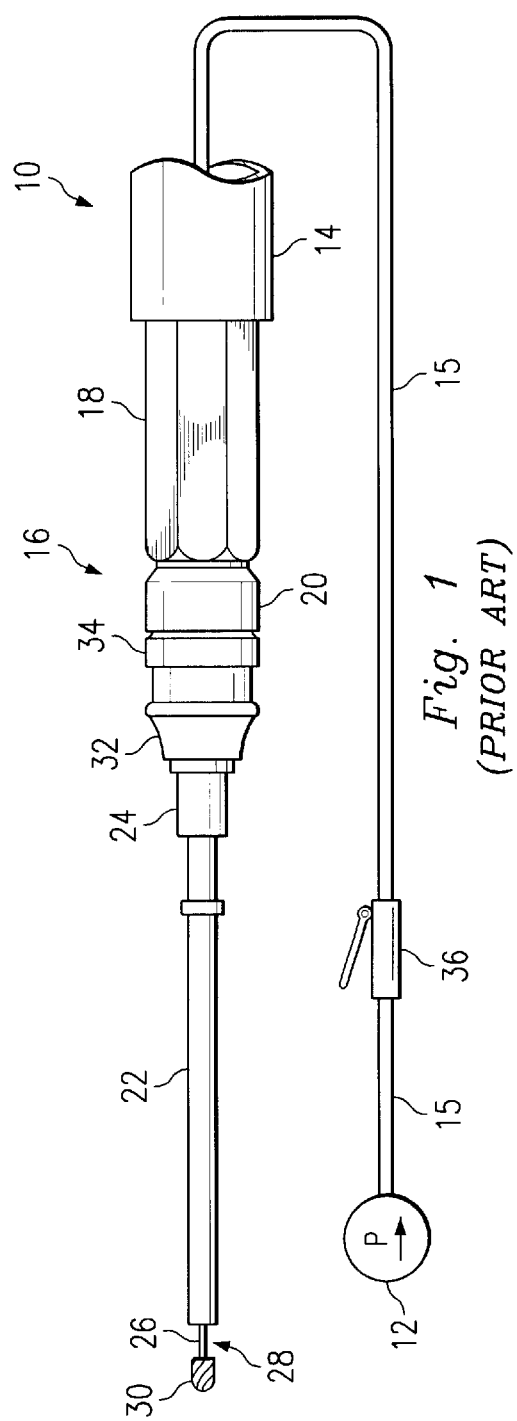
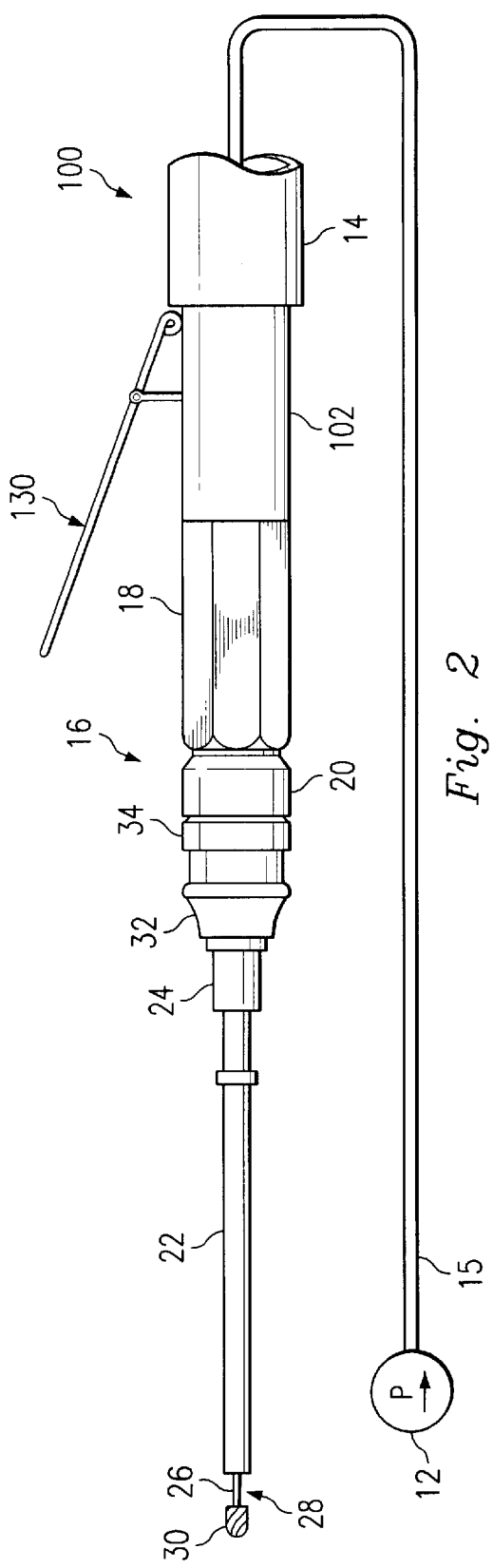

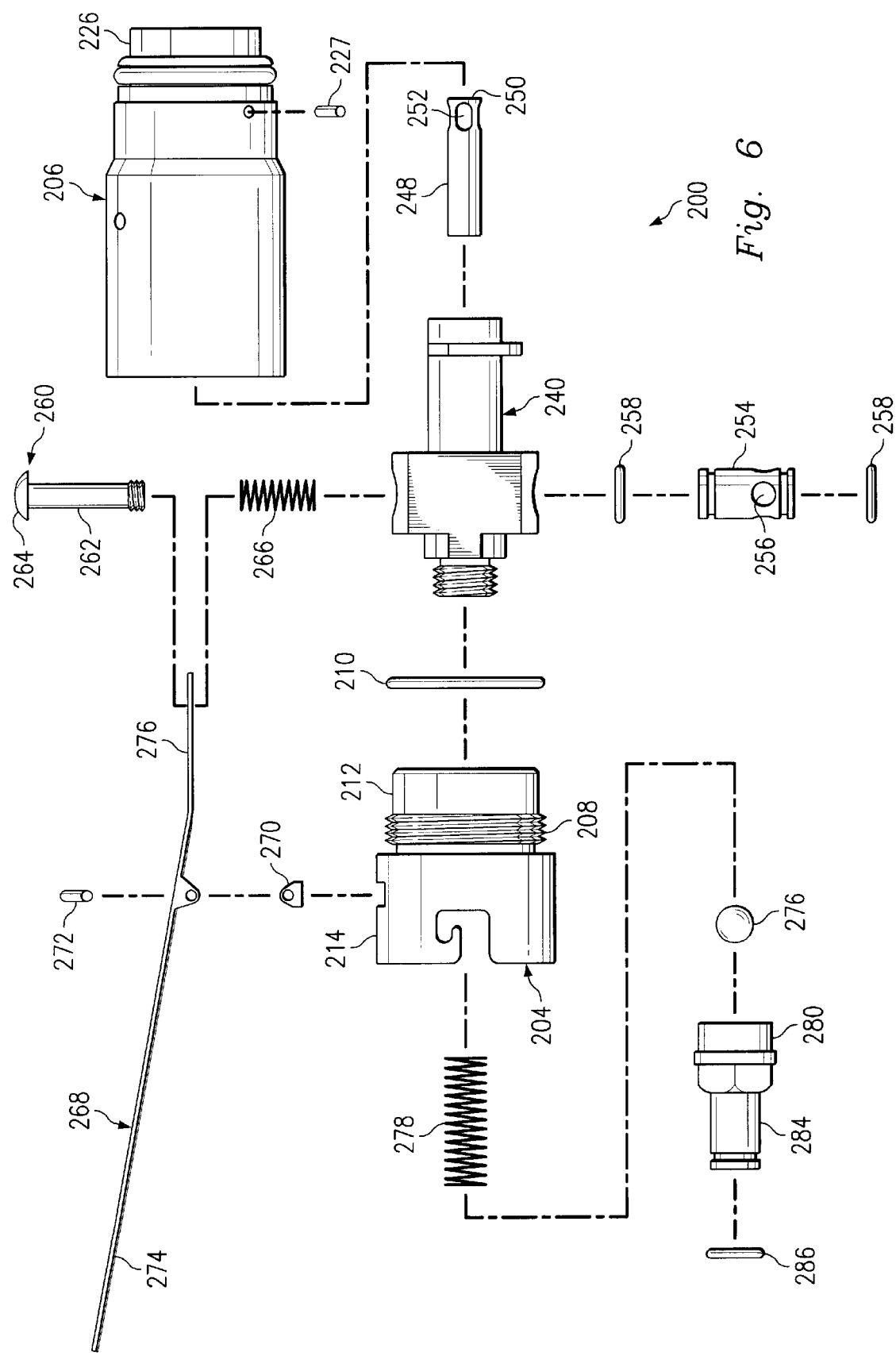

MODULAR HAND CONTROL FOR PNEUMATIC RESECTING TOOL

BACKGROUND OF THE INVENTION

1. Field of the Invention

The present invention relates generally to surgical instruments used for the resectioning of bone or other tissue. In other aspects, the present invention relates to methods and devices for actuating such surgical instruments. In one particular aspect, the present invention relates to a modular hand-control for use with a pneumatic resecting tool.

2. Description of the Related Art

Surgical instruments employing fluid-powered motors to rotate cutting or resectioning tools are conventional and well-known in the art. Such surgical tools are used in such delicate surgical operations as brain surgery and microsurgery. These surgical instruments must be capable of sanitary operation without contaminating an operating room environment. Also, because of the delicate nature of surgery, the surgical instrument must be manipulated easily by the surgeon without causing undue fatigue, which could lead to disastrous surgical errors.

Pneumatic resecting tools of this type are disclosed, for example, in U.S. Pat. Nos. 5,549,634; 5,352,234; 5,505,737; 5,569,256; 5,439,005; and 5,741,263. Traditionally, these tools are part of a tool system in which the tool is actuated using a foot pump or foot valve which a surgeon operates with his foot. The foot pump is typically located proximate the air pump that provides fluid pressure to operate the tool.

There are a number of surgical instrument systems that incorporate hand-operated controls for the instrument. Examples of such systems are discussed in U.S. Pat. Nos. 3,712,386; 3,752,241; 4,530,357; 5,478,093 and Re. 27,032. However, these systems do not permit the hand control to be disconnected from the surgical instrument. Thus, the hand-operated control cannot be removed from the system when it is desired not to use it.

Quick release couplings are also known for use with surgical instruments such as this. Examples of these type of release couplings are found in U.S. Pat. Nos. 5,505,737; 5,569,256 and 5,741,263. However, these devices are intended for releasably securing a cutting tool to the spindle shaft of a drive motor. In other words, they are useful for interconnecting the working end of the tool with the motor, thus providing a means of, for example, quickly changing out the tools during operation. They are not, however, designed to provide an interconnection between the motor section and the air conduit for the instrument. Nor do they provide any means for operably associating a hand-operated control with the tool.

Some surgeons may, however, prefer to use a hand-operated control rather than a foot-operated control. Where it is desired to begin using foot control, rather than hand control, there is an advantage to removing, or disabling, the hand control, to prevent inadvertent operation or interruptions in operation, of the surgical tool.

Therefore, a need exists for devices and methods that permit the quick and easy interconnection of a hand-control for resecting tools and similar devices.

SUMMARY OF INVENTION

The present invention provides methods and apparatus for a modular device control to be rapidly and easily installed in a resecting tool system. The motor portion of the resecting tool can be readily separated from the air conduit to which it is attached. In a preferred embodiment, modular hand-operated control is then inserted between the air conduit and motor and interconnected with both components. The modular hand-control provides a housing with an actuatable lever, or handle, which controls an internal valve assembly. Preferably, the hand control can be operably associated with the tool system by using quick releases.

BRIEF DESCRIPTION OF THE DRAWINGS

FIG. 1 is a schematic view of a prior art resecting tool system showing a resecting tool having a motor interconnected with the air conduit.

FIG. 2 depicts a preferred embodiment of a surgical instrument system of the present invention wherein a modular hand-control has been installed between the air conduit and motor component.

FIG. 6 provides an exploded view of the hand control shown in FIG. 4.

DETAILED DESCRIPTION OF THE PREFERRED EMBODIMENTS

Figure 3:
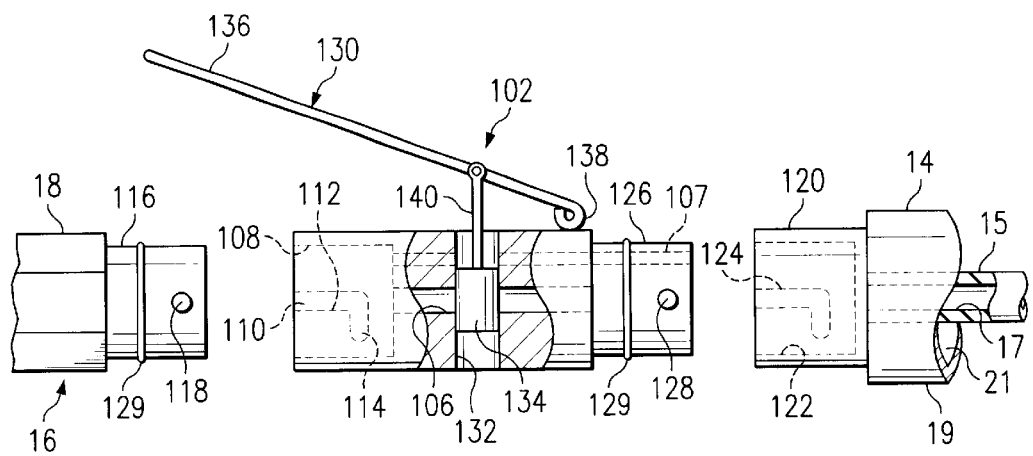
FIG. 3 is an exploded view, partially in cross-section, showing portions of the system depicted in FIG. 2 in which one embodiment of a modular hand-control is employed.

Referring first to FIG. 1, an exemplary prior art surgical tool system 10 is shown schematically. The system 10 includes an air pump or fluid pump 12 associated with an air or fluid conduit 14 to provide pressurized air to a surgical instrument or tool 16, which is shown in enlarged detail in FIGS. 1 and 2. It is noted that the air conduit 14 is coaxial having an inner conduit, or liner, that defines a passageway that provides pressurized fluid from the pump 12 to the surgical instrument 16 and an outer conduit, or liner that returns fluid from the instrument 16 to the pump 12.

The surgical instrument 16 includes a motor 18 that is affixed to the air conduit 14 by means of threading or pinning (not shown). A base 20 is affixed to the motor 18 by a threaded connection (not shown) as well. A support sleeve 22 extends from and is joined at an end 24 of the base 20. The support sleeve 22 houses the tool shaft 26 of a resecting tool 28. At one end of the resecting tool 28 is a cutting element 30. The cutting element 30 can be a burr, saw blade or drill used in the cutting or removal of tissue. The sleeve 22 may be provided with internal bearings (not shown) to support the tool shaft 26 as the resecting tool 28 is rotated.

Mounted around the base 20 is a sleeve engagement collar 32. The sleeve engagement collar 32 is longitudinally moveable relative to the base 20 and is provided with an annular, lower facing shoulder (not shown). Positioned below the collar 32 is a cylindrical spring housing 34 that surrounds and is joined at its lower end to the base 20. The wall of the spring housing 34 is spaced apart from the exterior of the base 20 to define and annular space (not shown) for receiving the lower end of an outer coiled spring (also not shown) which surrounds the base 20. The collar 32 has a lower cylindrical portion or skirt (not shown) which surrounds the upper end of the coiled spring and is received within the spring housing 34. The skirt of the collar 32 is able to slide within the spring housing 34 for a distance as the collar 32 is moved in relation to the base 20. It is noted that the collar 32 and spring housing 34, as well as the coiled spring and associated components, are part of a release arrangement that permits rapid changing out of the resecting tool 28 during operation of the surgical instrument 16. This type of tool-changing release arrangement, as well as further details concerning operation of the exemplary surgical instrument 16 is described in greater detail in U.S. Pat. No. 5,505,737 issued to Gosselin et al. This arrangement is mentioned here merely for the sake of completeness. It is noted that the use of this or any release arrangement for the removal or replacement of the resecting tool 28 from the motor portion 18 of the surgical instrument 16 is not necessary to the invention and is merely described as background for the present invention.

A foot-operated control valve 36 is shown incorporated into the conduit 14 so that a surgeon or other individual can actuate the tool 16 by depressing the valve 36. The valve 36 is securely, and perhaps permanently, associated with the conduit 14 so that it cannot be readily removed.

Referring now to FIG. 2, a preferred embodiment of an improved resecting tool system 100 is shown. For simplicity and clarity, like components between the two described surgical tool systems are numbered alike. Although not shown in FIG. 2, a foot-operated control, such as the control 36 shown in FIG. 1, may or may not be present along conduit 14.

A first exemplary embodiment of a modular hand control 102 is shown between the motor assembly 18 and the conduit 14. The conduit 14, as illustrated by FIG. 3, has an inner liner 15 that defines an inner passage 17 through which pressurized fluid is transmitted from the pump 12 toward the instrument 16. The inner liner 15 is surrounded by an outer liner 19 that defines an outer passage 21 through which fluid can be communicated back to the pump 12.

Figure 4:
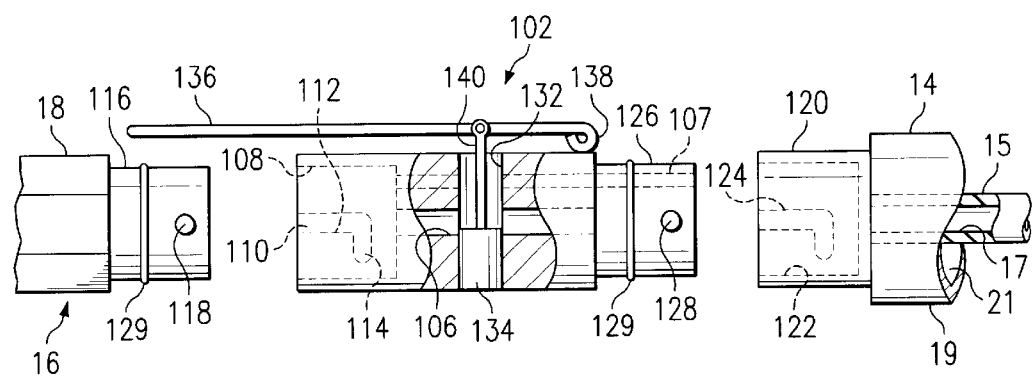
FIG. 4 is cross-sectional view of the hand control shown in FIG. 3 wherein the control has been actuated to permit fluid flow through the control.

The hand control 102 is shown in greater detail in FIGS. 3 and 4 and can be seen to have a central cylindrical housing 104 with a central fluid flowbore 106 defined therein and disposed longitudinally therethrough. A second, peripheral fluid flowbore 107 is also disposed longitudinally through the housing 104, but is not centrally located within the housing. It should be understood that there may be more than one such peripheral fluid flowbore 107, or the peripheral flowbore 107 may be semicircular in shape so that the flowbore 107 is not blocked by elements of the valve, including piston 134 which will be described.

A receptacle 108 is formed in a first end of the housing 104 and contains a groove 110 milled upon its internal wall. The groove 112 is L-shaped so that a longitudinal portion 112 and a lateral portion 114 are provided. The receptacle 108 is shaped and sized to receive the complementary-shaped pin connector 116 that extends from the motor assembly 18. A lug 118 extends radially from the pin connector 116. The lug 118 is shaped and sized so as to be slidably received within the groove 112 of the receptacle 108.

A cylindrical fitting 120 is securely affixed to the conduit 14 and contains a receptacle 122 and milled L-shaped groove 124 which are formed in the same manner as the receptacle 108 and groove 110 described earlier. It is preferred that the receptacle 122 and groove 124 have essentially the same dimensions and size as the receptacle 108 and groove 110, as well.

A pin connector 126 is formed in the longitudinal end of the housing 104 opposite the receptacle 108 of the hand control 102. A lug 128 extends radially from the pin connector 126. The lug 128 is shaped and sized to be slidably received within the groove 124 of the receptacle 122. Again, it is preferred that the pin connector 126 and lug 128 be essentially the same size and shape as the pin connector 116 and lug 118, respectively. The similar sizing of the pin connectors and receptacles, as well as the grooves and lugs, permits the motor assembly 18 of the tool 16 to be affixed either to the modular hand control 102 or else directly to the fitting 120 of the air conduit 14. Additionally, the fitting 120 can be affixed either to the hand control 102 or directly to the motor assembly 18.

It is also noted that elastomeric O-rings 129 may be present on the pin connectors 116, 126 in order to help create fluid sealing of the components.

A valve assembly, shown generally at 130, is operable to control the flow of air or other fluid from the pump 12 to the tool 16. The valve assembly 130 includes a piston passageway 132 that is disposed through the housing 104. A piston 134 is reciprocably disposed within the passageway 132 so that it can selectively block the flow of fluid through the flowbore 106. A lever 136 is pivotally connected to the housing 104 at a pivot point 138. A linkage 140 interconnects the lever 136 to the piston 134 so that the piston 134 is moved within the passageway 132 as the lever 136 is pivoted about the pivot point 138. It is preferred that there be a spring (not shown), such as a torsional spring, that biases the lever 136 into a position away from the housing 136 so that the piston 134 is located so as to block the flow of air through the flowbore 106 toward the tool 16. When the lever 136 is pushed downwardly (preferably by hand), toward the housing 104, the piston 134 is moved within the passageway 132 so that fluid flow through the flowbore 106 is no longer blocked and the motor 18 of the tool 16 will function to operate the tool 16 as shown in FIG. 4. Thus, the tool 16 can be selectively operated by operating the valve assembly 130 of the hand control 102.

During operation, the modular hand control 102 may be rapidly installed or removed from the tool system 100. To install the hand control 102, the motor section 18 of the tool 16 is affixed to the hand control 102 by disposing the pin connector 116 within the receptacle 108. The lug 118 is slidingly disposed into the longitudinal portion 112 of the groove 110. The motor section 18 can be securely locked to the hand control 102 by rotating the motor section 18 with respect to the hand control 102 so that the lug 118 becomes disposed within the lateral portion 114 of the groove 110. Next, the pin connector 116 is affixed in a locking relation to the fitting 120 of the air conduit 14 in a similar manner. When the hand control 102 is affixed in this manner, the central longitudinal passageway 106 of the housing 104 is aligned with and adjoins inner passage defined by the inner liner 15 of the conduit 14. The longitudinal passageway 107 of the housing 104 is aligned with and adjoined with the outer passage 21 defines by the outer liner 19 of the conduit 14. As a result, pressurized fluid from the pump 12 is directed from the inner passage 17 into the central passageway 106 of the housing 104 and, then to the instrument 16. Fluid returning from the instrument 16 toward the pump 12 is directed through the longitudinal passageway 107 in the housing 104 and then into the outer passage 21 whereby it can return to the pump 12.

The modular hand control 102 may be readily removed from the tool system 100. This can be done if it is desired to control operation of the tool 16 by some other means, such as by a foot valve (not shown). In order to remove the control 102 from the system 100, the control 102 is rotated with respect to the fitting 120 and the motor assembly 18 so that the lugs 118, 128 are released from the lateral portions of the grooves 110, 124. The connections provided between these components are quick release connections since they do not require time-consuming operations such as the unthreading of threaded connections or the removal of separate pins.

Figure 5:
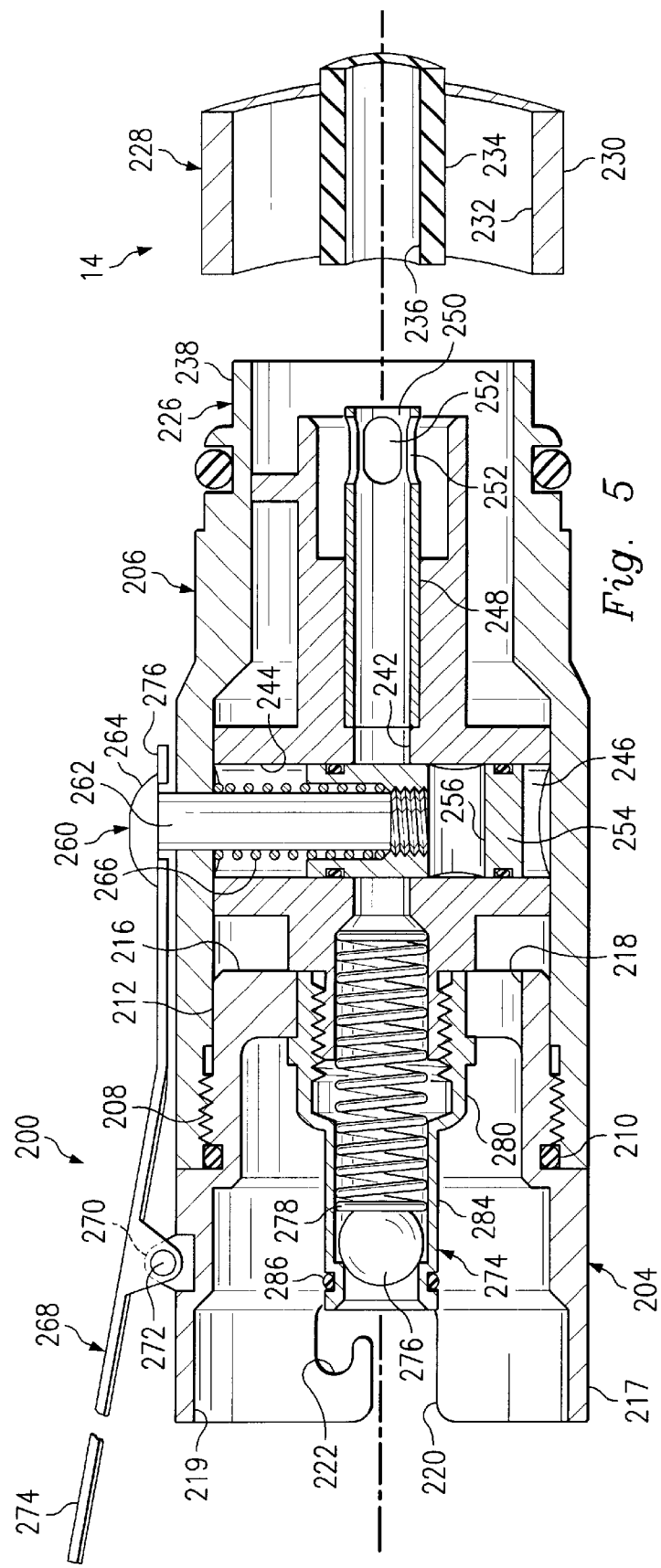
FIG. 5 is a cross-sectional view of an alternative embodiment of a modular hand control constructed in accordance with the present invention.

Referring now to FIGS. 5 and 6, an alternate exemplary embodiment is depicted for a hand control 200 constructed in accordance with the present invention. This hand control 200 shares many of the same features provided by the hand control 102 described earlier, but also incorporates a check valve assembly designed to prevent unwanted release of fluid pressure when the components of the system are disconnected. The hand control 200 also includes an outer fluid flow passageway for fluid so that the control can be used with coaxial fluid pressure conduits that provide a return passageway whereby fluid is returned from the tool to the air pump 12.

The hand control 200 includes an outer housing 202 that is formed from first and second housing sections 204, 206. The first housing section 204 fits within and is threadedly affixed to the second housing section 206 by threaded connection 208. An elastomeric O-ring 210 is secured within the threaded connection 208 to assist in creating a fluid seal. The first housing section 204 features a reduced diameter portion 212 and an expanded diameter portion 214. The reduced diameter portion 212 provides an inwardly-directed annular flange 216 (visible in FIG. 4) with a fluid communication port 218 disposed therethrough. The expanded diameter portion 214 includes a receptacle 219 and a groove 220 which is cut into the material forming the expanded diameter portion 214. As with the grooves 110, 124 described earlier, the groove 220 provides a lateral portion 222 within which a suitably sized and shaped lug can reside.

The second housing section 206 includes a receptacle 224 within which the reduced portion 212 of the first housing resides. A coaxial pin connector 226 is provided at the opposite end of the second housing section 206 and is adapted to have a coaxial air conduit 228 (shown in FIG. 5) slipped on to it to form a connection. A lug 227 (visible in FIG. 6) extends radially outwardly from the connector 226.

As is apparent from FIG. 4, the coaxial conduit 228 is made up of an outer conduit member 230 that defines an outer airflow passage 232 and a coaxially-located inner conduit member 234 that defines an inner airflow passage 236 therein.

A valve body 240 is retained within the receptacle 224 between the first and second housing section 204, 206 when they are assembled. The valve body 240 defines a longitudinal fluid flowbore 242 and a vertical valve chamber 244. Fluid apertures 246 are provided around the periphery of the valve body 240 so that fluid within the receptacle 224 can be communicated across the valve body 240 and into the pin connector 226.

A valve stem 248 is secured to the valve body 240 by threading or another secure means of affixation. The valve stem 248 includes both an axial fluid opening 250 and radial fluid openings 252.

The valve chamber 244 houses a valve spindle 254 that contains a lateral fluid port 256. O-rings 258 ensure fluid sealing between the spindle 254 and the chamber 244. An actuator pin 260 is secured by threaded connection to the valve spindle 254. The actuator pin 260 includes an elongated shaft 262 and an enlarged head 264. A spring 266 surrounds the shaft 262 to bias the valve spindle 254 to a lower position within the valve chamber 244. When so biased, the spindle 254 blocks fluid passage through the passageway 242.

An actuator lever 268 is secured by pintle 270 and pin 272 to the first housing section 204. The actuator lever 268 has a proximal end 274 adapted to be engaged by a hand and a distal end 276 for operation of the actuator pin 260. The actuator pin 260 passes through lo the distal end 276 of the lever 268 so that the distal end 276 is disposed beneath the enlarged head 264 of the actuator pin 260 such that when the lever 268 is pivoted about the pivot pin 272, the actuator pin 260 and valve spindle 254 are moved upwardly within the valve chamber 244 so that the fluid port 256 becomes aligned with the fluid passageway 246, thereby permitting fluid to be communicated across the valve body 240.

A check valve assembly 274 is incorporated into the hand control 200 so that unwanted fluid escape from the inner airflow passage 236 does not occur when the components are disconnected from one another. The check valve assembly 274 includes a check ball 276 that is biased by spring 278 against a valve seat 280. The valve seat 280 is affixed to the valve body 240 to retain the spring 278 and check ball 276 within a check valve chamber 282. The valve seat 280 presents a nipple-type fitting 284 adapted to engage a portion of the motor 18 of instrument 16 by a complimentary interference fit. An O-ring 286 assists in fluid sealing.

In operation, the check ball 276 is normally biased by the spring 278 and by fluid pressure against the valve seat 280. Therefore, fluid is blocked from exiting the valve seat 280 by the check ball 276. However, when the nipple-type fitting 284 of the valve seat 280 is engaged with the motor 18, a central protruding portion of the motor 18 will contact the check ball 276 to push it off of the valve seat 280, thus permitting fluid to pass through the check valve assembly 274. As a result of the check valve assembly 274, pressurized fluid can only escape the hand control 200 when the hand control 200 is affixed to the motor 18.

The coaxial pin connector 226 is made up of the outer sleeve 238 of the second housing section 206 and the valve stem 248 which is retained therein. The pin connector 226 is adapted to interconnect with the air conduit 14 of the system so that the valve stem 248 engages the inner liner 234 of the coaxial conduit 228 and the outer sleeve 238 engages the outer liner 230 of the coaxial conduit 228, thus permitting coaxial air flow between the two components.

Other embodiments could include distal or proximal swivels in the modular hand control assembly or in the adjacent assembly to prevent binding or kinking. While the invention has been shown in only one of its forms, it should be apparent to those skilled in the art that it is not so limited, but it is susceptible to various changes without departing from the scope of the invention.

What is claimed is:

1. A modular control to actuate a motorized fluid pressure operated surgical instrument, the hand-control comprising:
   a housing defining a fluid flow bore therethrough;
   a valve which is actuatable to control fluid flow through the flowbore;
   a first connector to be removably affixed to a motorized surgical instrument, thereby providing fluid to the surgical instrument for operation of a motor in the surgical instrument; and
   a second connector for connection of the housing to a fluid pressure source.

2. The control of claim 1 further comprising a valve assembly for selectively blocking the flow of fluid through the flowbore.

3. The control of claim 2 further comprising a hand-operated lever for control of the valve assembly.

4. The control of claim 1 wherein the first and second connectors further comprise quick release connectors.

5. A surgical cutting tool system comprising:
   a fluid pressure source;
   a fluid pressure conduit operably interconnected to the fluid pressure source;
   a surgical cutting tool having a motor therein; and
   a modular component for controlling the flow of fluid pressure from the fluid pressure source to the motor of the cutting tool, the modular component adapted to be removably associated with the cutting tool for selective fluid pressure control of said motorized cutting tool.

6. The system of claim 5 wherein the modular component comprises a valve assembly that is removably affixed to the cutting tool.

7. The system of claim 6 wherein the valve assembly comprises a pivotable lever associated with a piston for selective movement of the piston into and out of a position blocking fluid flow to the cutting tool.

8. The system of claim 5 further comprising a connector for connecting the modular component to the fluid pressure conduit.

9. The system of claim 5 further comprising a connector for connecting the modular component to the cutting tool.

10. A control assembly kit having component parts capable of being assembled to operably associate a control device with a surgical instrument system having a fluid pressure source and a surgical instrument, the kit comprising:
    a control device operable to control flow of fluid pressure from the fluid pressure source to a surgical instrument when operably associated with a fluid pressure source and a surgical instrument, the control device having first and second connector members adapted to be interconnected with complimentary connectors;
    a third connector member associated with a surgical instrument and adapted to be removably affixed to the first connector member to operably associate the control device with a surgical instrument; and
    a fourth connector member associated with a fluid pressure source and adapted to be removably affixed to the second connector member to operably associate the control device with a fluid pressure source.

11. The kit of claim 10 wherein the control device comprises a valve assembly to control flow of fluid pressure from the fluid pressure source to the surgical instrument.

12. The kit of claim 10 wherein the first connector comprises a receptacle and the third connector comprises a pin connector shaped and sized to be received within the receptacle.

13. The kit of claim 12 wherein the third connector further comprises a radially projecting lug and the first connector further comprises a groove which is formed to be substantially complimentary to the lug so as to receive it in sliding relation.

14. The kit of claim 13 wherein the groove is substantially L-shaped to provide a lateral portion within which the lug can reside in order to secure the first and third connectors in a locking relation.

15. The kit of claim 10 wherein the third connector may also be removably affixed to the fourth connector.

16. The kit of claim 15 wherein the third connector comprises a pin connector and the fourth connector comprises a receptacle shaped and sized to receive the pin connector.

17. The kit of claim 16 wherein the third connector further comprises a radially projecting lug and the fourth connector further comprises a groove which is formed to be substantially complimentary to the lug so as to receive it in sliding relation.

18. The kit of claim 17 wherein the groove is substantially L-shaped to provide a lateral portion within which the lug can reside in order to secure the first and third connectors in a locking relation.

19. The kit of claim 10 wherein the control device comprises a valve assembly which can be actuated to control fluid pressure flow from the fluid pressure source to the surgical instrument.

20. The kit of claim 19 wherein the valve assembly comprises a lever to actuate a valve within the valve assembly.

21. A controller for insertion into a surgical system, wherein the surgical system includes a motorized surgical instrument having a first connector for operatively coupling the motor with a pressurized fluid source via a hose having a second connector operable to engage the first connector, the controller comprising:
    an adaptive housing operable to control fluid flow from the pressurized fluid source to the surgical instrument;
    a third connector operable to engage the first connector; and
    a fourth connector operable to engage the second connector.

22. The controller of claim 21 further comprising a valve assembly operable to control fluid flow through the housing.

23. The controller of claim 22 further comprising a hand-operated lever for actuating the valve assembly.

24. The controller of claim 21 wherein the first and fourth connectors are female and the second and third connectors are male.

25. The controller of claim 21 wherein the first and fourth connectors are male and the second and third connectors are female.

26. The controller of claim 21 wherein the first, second, third, and fourth connectors comprise quick release couplings.

27. The controller of claim 21, wherein the first connector is substantially identical to the fourth connector and the second connector is substantially identical to the third connector.

28. The controller of claim 21 wherein said adaptive housing and the motorized surgical instrument form a substantially rigid combination when said third connector engages the first connector.

29. A surgical system comprising:
    a motorized surgical instrument comprising a first connector in fluid communication with the motor;
    a hose operatively associated with a fluid pressure source for providing pressurized fluid to the motor, the hose including a second connector; and
    a controller operable to control fluid flow from the fluid pressure source to the surgical instrument, the controller comprising a third connector operable to engage the first connector and a fourth connector operable to engage the second connector,
    wherein the system has a first operable configuration comprising said first connector operably connected to said second connector and a second operable configuration comprising said first connector operably connected to said third connector and said second connector operably connected to said fourth connector.

30. The system of claim 29 wherein the first and fourth connectors are female and the second and third connectors are male.

31. The system of claim 29 wherein the first and fourth connectors are male and the second and third connectors are female.

32. The system of claim 29, wherein said motorized surgical instrument and said controller form a substantially rigid combination in said second configuration.

* * * * *